(12) United States Patent
Zadini et al.

(10) Patent No.: US 8,952,067 B2
(45) Date of Patent: Feb. 10, 2015

(54) SUBCUTANEOUS FAT REDUCTION

(75) Inventors: Filiberto Zadini, Camarillo, CA (US); Giorgio Zadini, legal representative, Camarillo, CA (US); Boris Ratiner, Tarzana, CA (US)

(73) Assignee: Atheronova Operations, Inc., Irvine, CA (US)

( * ) Notice: Subject to any disclaimer, the term of this patent is extended or adjusted under 35 U.S.C. 154(b) by 0 days.

(21) Appl. No.: 13/528,772

(22) Filed: Jun. 20, 2012

(65) Prior Publication Data

US 2013/0012590 A1 Jan. 10, 2013

Related U.S. Application Data

(60) Provisional application No. 61/498,972, filed on Jun. 20, 2011.

(51) Int. Cl.
| | | |
|---|---|---|
| *A01N 47/28* | (2006.01) | |
| *A61K 31/17* | (2006.01) | |
| *A61K 33/40* | (2006.01) | |
| *A61K 36/534* | (2006.01) | |
| *A61K 31/015* | (2006.01) | |

(52) U.S. Cl.
CPC ............ *A61K 31/015* (2013.01); *A61K 31/17* (2013.01); *A61K 33/40* (2013.01); *A61K 36/534* (2013.01)
USPC ...................................................... 514/588

(58) Field of Classification Search
None
See application file for complete search history.

(56) References Cited

U.S. PATENT DOCUMENTS

| | | | | |
|---|---|---|---|---|
| 6,323,166 | B1 * | 11/2001 | Kamiya | 510/119 |
| 2003/0008018 | A1 * | 1/2003 | Miller et al. | 424/616 |
| 2007/0071706 | A1 | 3/2007 | Zadini et al. | |
| 2008/0015249 | A1 * | 1/2008 | Bessette et al. | 514/456 |
| 2008/0107679 | A1 | 5/2008 | Dilallo et al. | |
| 2008/0107742 | A1 | 5/2008 | Hare | |
| 2008/0119559 | A1 * | 5/2008 | Weissbach et al. | 514/569 |
| 2009/0214628 | A1 | 8/2009 | de Rijk | |
| 2009/0217398 | A1 | 8/2009 | Al Murrani et al. | |

FOREIGN PATENT DOCUMENTS

WO    WO-2006/102439 A2    9/2006

OTHER PUBLICATIONS

Jones (Applications of Hydrogen Peroxide and Derivatives, The Royal Society of Chemistry, 1999, Chapter 2, p. 40).*

* cited by examiner

*Primary Examiner* — Dennis Heyer
*Assistant Examiner* — Daniel M Podgorski
(74) *Attorney, Agent, or Firm* — James W. Hill; McDermott Will & Emery LLP

(57) ABSTRACT

Topical dermatological preparations including one or more lipodissolving, lipolytic, or adipocyte-disrupting substances for treatment of localized adiposity can include carbamide peroxide and a terpene such as d-limonene. In some embodiments, the preparations can include carbamide peroxide as a first component and, as a second component, at least one peppermint oil terpene, peppermint oil, or a compound isolated or derived from peppermint oil.

5 Claims, No Drawings

SUBCUTANEOUS FAT REDUCTION

RELATED APPLICATIONS

This application claims the priority benefit of U.S. Provisional Application No. 61/498,972, filed Jun. 20, 2011, the entirety of which is incorporated herein by reference.

FIELD

The subject technology generally relates to compositions and methods for treating localized adiposity and, in some embodiments, includes topical dermatological preparations for reducing fat volume in a body.

BACKGROUND

The skin is a coating organ covering the body's surface. It is a vital organ enabling multiple functions such as sensing functions, protection from external aggressions, as well as immunological, metabolic, and thermoregulatory functions. These roles are made possible due to a complex structure including three distinct, superimposed layers: epidermis, dermis, and hypodermis. The epidermis is a coating epithelium that constitutes the external structure of the skin and provides its function of protection. This function is provided by the cohesion of epithelial cells and by the production of a filamentous and resistant protein, keratin.

The dermis is a connective tissue made up of a ground substance in which fibroblasts reside along with collagen fibers and elastin fibers, which are fibrous protein synthesized by fibroblasts. The collagen fibers ensure a great part of the solidity of the dermis; they take part in the elasticity and especially in the tonicity of the skin and/or the mucous membranes.

Below the dermis is a layer of adipose tissue: hypodermis, or subcutaneous tissue. The hypodermis includes a reserve fat layer, or white adipose tissue, attached to the lower part of the dermis by expansions of collagens and elastic fibers. The reserve fat layer consists of large vacuolated cells, the adipocytes, almost entirely filled with triglycerides. The volume of these cells can change rapidly, during a weight loss or weight gain, and can measure from 40 to 120 µm in diameter, which corresponds to a variation of 27 times in volume. The adipose tissue also contains connective tissue in which can be found, inter alia, particular fibroblasts and preadipocytes. The adipose tissue can store lipids as triglycerides or release them as fatty acids and glycerol.

Various conditions such as obesity, aging, and illnesses (e.g., HIV infection) can cause changes in body fat distribution which can result in abnormal and localized subcutaneous fat accumulation that can be disfiguring and, in some cases, cause impairment of breathing or other bodily functions. Numerous nonsurgical professed treatments, topical and non topical, are available today for alleged treatment of localized subcutaneous fat deposits. However, some of these professed treatments have a scientific, empiric base, and some a pseudoscientific base. Among the topical professed treatments, only the professed treatments delivered via intradermal injections of lipolytic compounds have achieved clinically satisfactory results. Topical treatments based on transdermal delivery of medications using methods other than percutaneous injections have a high rate of failure.

SUMMARY

Despite the availability of some professed means for treating localized subcutaneous fat deposits, there is a continuing need for a new compositions and methods for disrupting or reducing localized subcutaneous fat deposits.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 6. The other clauses can be presented in a similar manner.

In one aspect, the invention relates to a therapeutic formulation comprising carbamide peroxide and d-limonene, the formulation configured for administration to adipose tissue of a subject.

The formulation may be an amount effective to induce adipolysis at a target site in the subject.

The formulation may comprise from about 1% to about 50% by weight carbamide peroxide, based on the total weight of the formulation.

The formulation may comprise from about 1% to about 50% by weight d-limonene, based on the total weight of the formulation.

The formulation may be in the form of an aqueous solution, a hydroalcoholic solution, an oil-in-water emulsion, a water-in-oil emulsion, a multiple emulsion, a cream, a suspension, a powder, a lotion, a milk, a serum, a pomade, a gel, a paste, a foam, or a transdermal patch.

The formulation may further comprise at least one of a pharmaceutically acceptable carrier or diluent.

In another aspect, the invention relates to a method of inducing adipolysis at a target site in a subject, comprising: administering to the target site a therapeutically effective amount of a formulation comprising carbamide peroxide and d-limonene.

The formulation may be administered by injecting the therapeutically effective amount of the formulation at the target site.

The administration may comprise multiple injection sessions.

In another aspect, the invention relates to a therapeutic formulation comprising carbamide peroxide and peppermint oil or a compound isolated or derived from peppermint oil, the formulation configured for administration to adipose tissue of a subject.

The formulation may be in an amount effective to induce adipolysis at a target site in the subject.

The formulation may comprise from about 25% to about 75% by weight carbamide peroxide, based on the total weight of the formulation.

The formulation may comprise from about 25% to about 75% by weight peppermint oil or a compound isolated or derived from peppermint oil, based on the total weight of the formulation.

The compound isolated or derived from peppermint oil may comprise at least one of menthol, menthone, menthyl acetate, isomenthone, menthofuran, cineole, pulegone, limonene, isopulegol, or carvone.

The formulation may be in the form of an aqueous solution, a hydroalcoholic solution, an oil-in-water emulsion, a water-in-oil emulsion, a multiple emulsion, a cream, a suspension, a powder, a lotion, a milk, a serum, a pomade, a gel, a paste, a foam, or a transdermal patch.

The formulation may further comprise at least one of a pharmaceutically acceptable carrier or diluent.

In another aspect, the invention relates to a method of inducing adipolysis at a target site in a subject, comprising:

administering to the target site a therapeutically effective amount of a formulation comprising carbamide peroxide and peppermint oil or a compound isolated or derived from peppermint oil.

The formulation may comprise from about 25% to about 75% by weight carbamide peroxide, based on the total weight of the formulation.

The formulation may comprise from about 25% to about 75% by weight peppermint oil or a compound isolated or derived from peppermint oil, based on the total weight of the formulation.

The compound isolated or derived from peppermint oil may comprise at least one of menthol, menthone, menthyl acetate, isomenthone, menthofuran, cineole, pulegone, limonene, isopulegol, or carvone.

The formulation may be administered by injecting the therapeutically effective amount of the formulation at the target site.

The administration may comprise multiple injection sessions.

In another aspect, the invention relates to a therapeutic formulation comprising carbamide peroxide and at least one peppermint oil terpene, the formulation configured for administration to adipose tissue of a subject.

The formulation may be in an amount effective to induce adipolysis at a target site in the subject.

The formulation may comprise from about 50% to about 99% by weight carbamide peroxide, based on the total weight of the formulation.

The formulation may comprise from about 50% to about 99% by weight at least one peppermint oil terpene, based on the total weight of the formulation.

The at least one peppermint oil terpene may be at least one of menthol, menthone, isomenthone, menthofuran, cineole, limonene, or carvone.

The formulation may be in the form of an aqueous solution, a hydroalcoholic solution, an oil-in-water emulsion, a water-in-oil emulsion, a multiple emulsion, a cream, a suspension, a powder, a lotion, a milk, a serum, a pomade, a gel, a paste, a foam, or a transdermal patch.

The formulation may further comprise at least one of a pharmaceutically acceptable carrier or diluent.

In another aspect, the invention relates to a method of inducing adipolysis at a target site in a subject, comprising: administering to the target site a therapeutically effective amount of a formulation comprising carbamide peroxide and at least one peppermint oil terpene.

The formulation may comprise from about 50% to about 99% by weight carbamide peroxide, based on the total weight of the formulation.

The formulation may comprise from about 50% to about 99% by weight of at least one peppermint oil terpene, based on the total weight of the formulation.

The at least one peppermint oil terpene may be one of menthol, menthone, isomenthone, menthofuran, cineole, limonene, or carvone.

The formulation may be administered by injecting the therapeutically effective amount of the formulation at the target site.

The administration may comprise multiple injection sessions.

In another aspect, the invention relates to a therapeutic formulation comprising carbamide peroxide and at least one terpene, the formulation configured for administration to adipose tissue of a subject.

The formulation may be in an amount effective to induce adipolysis at a target site in the subject.

The formulation may comprise from about 1% to about 50% by weight carbamide peroxide, based on the total weight of the formulation.

The formulation may comprise from about 1% to about 50% by weight at least one terpene, based on the total weight of the formulation.

The terpene may be at least one of d-limonene, menthol, menthone, isomenthone, menthofuran, cineole, limonene, carvone, tricyclene, α-pinene, terpinolene, carveol, amyl alcohol, nerol, β-santalol, citral, pinene, nerol, b-ionone, caryophillen, guaiol, anisaldehyde, cedrol, linalool, longifolene, anisyl alcohol, patchouli alcohol, α-cadinene, 1,8-cineole, ρ-cymene, 3-carene, ρ-8-mentane, trans-menthone, borneol, α-fenchol, isoamyl acetate, terpin, cinnamic aldehyde, ionone, geraniol, myrcene, nerol, citronellol, carvacrol, eugenol, carvone, α-terpineol, anethole, camphor, nerolidol, farnesol, phytol, carotene, squalene, thymol, tocotrienol, perillyl alcohol, borneol, simene, carene, terpenene, linalool, 1-terpene-4-ol, or zingiberene.

The formulation may be in the form of an aqueous solution, a hydroalcoholic solution, an oil-in-water emulsion, a water-in-oil emulsion, a multiple emulsion, a cream, a suspension, a powder, a lotion, a milk, a serum, a pomade, a gel, a paste, a foam, or a transdermal patch.

The formulation may further comprise at least one of a pharmaceutically acceptable carrier or diluent.

In another aspect, the invention relates to a method of inducing adipolysis at a target site in a subject, comprising: administering to the target site a therapeutically effective amount of a formulation comprising carbamide peroxide and at least one terpene.

The formulation may comprise from about 50% to about 99% by weight carbamide peroxide, based on the total weight of the formulation.

The formulation may comprise from about 50% to about 99% by weight of at least one terpene, based on the total weight of the formulation.

The terpene may be at least one of d-limonene, menthol, menthone, isomenthone, menthofuran, cineole, limonene, carvone, tricyclene, α-pinene, terpinolene, carveol, amyl alcohol, nerol, β-santalol, citral, pinene, nerol, b-ionone, caryophillen, guaiol, anisaldehyde, cedrol, linalool, longifolene, anisyl alcohol, patchouli alcohol, α-cadinene, 1,8-cineole, ρ-cymene, 3-carene, ρ-8-mentane, trans-menthone, borneol, α-fenchol, isoamyl acetate, terpin, cinnamic aldehyde, ionone, geraniol, myrcene, nerol, citronellol, carvacrol, eugenol, carvone, α-terpineol, anethole, camphor, nerolidol, farnesol, phytol, carotene, squalene, thymol, tocotrienol, perillyl alcohol, borneol, simene, carene, terpenene, linalool, 1-terpene-4-ol, or zingiberene.

The formulation may be administered by injecting the therapeutically effective amount of the formulation at the target site.

The administration may comprise multiple injection sessions.

In another aspect, the invention relates to a formulation comprising carbamide peroxide and d-limonene, for use in inducing adipolysis at a target site in a subject.

The formulation may comprise from about 25% to about 75% by weight carbamide peroxide, based on the total weight of the formulation.

The formulation may comprise from about 25% to about 75% by weight d-limonene, based on the total weight of the formulation.

The formulation may comprise an injectable preparation.

The formulation may be in the form of an aqueous solution, a hydroalcoholic solution, an oil-in-water emulsion, a waterin-oil emulsion, a multiple emulsion, a cream, a suspension, a powder, a lotion, a milk, a serum, a pomade, a gel, a paste, a foam, or a transdermal patch.

The formulation may further comprise at least one of a pharmaceutically acceptable carrier or diluent.

In one aspect, the invention relates to a formulation comprising carbamide peroxide and peppermint oil or a compound isolated or derived from peppermint oil, for use in inducing adipolysis at a target site in a subject.

The formulation may comprise from about 1% to about 50% by weight carbamide peroxide, based on the total weight of the formulation.

The formulation may comprise from about 1% to about 50% by weight peppermint oil or a compound isolated or derived from peppermint oil, based on the total weight of the formulation.

The compound isolated or derived from peppermint oil may comprise at least one of menthol, menthone, menthyl acetate, isomenthone, menthofuran, cineole, pulegone, limonene, isopulegol, or carvone.

The formulation may comprise an injectable preparation.

The formulation may be in the form of an aqueous solution, a hydroalcoholic solution, an oil-in-water emulsion, a water-in-oil emulsion, a multiple emulsion, a cream, a suspension, a powder, a lotion, a milk, a serum, a pomade, a gel, a paste, a foam, or a transdermal patch.

The formulation may further comprise at least one of a pharmaceutically acceptable carrier or diluent.

In another aspect, the invention relates to a formulation comprising carbamide peroxide and at least one peppermint oil terpene for use in inducing adipolysis at a target site in a subject.

The formulation may comprise from about 50% to about 99% by weight carbamide peroxide, based on the total weight of the formulation.

The formulation may comprise from about 50% to about 99% by weight of at least one peppermint oil terpene, based on the total weight of the formulation.

The at least one peppermint oil terpene may comprise at least one of menthol, menthone, isomenthone, menthofuran, cineole, limonene, or carvone.

The formulation may comprise an injectable preparation.

The formulation may be in the form of an aqueous solution, a hydroalcoholic solution, an oil-in-water emulsion, a water-in-oil emulsion, a multiple emulsion, a cream, a suspension, a powder, a lotion, a milk, a serum, a pomade, a gel, a paste, a foam, or a transdermal patch.

The formulation may further comprise at least one of a pharmaceutically acceptable carrier or diluent.

In another aspect, the invention relates to a formulation comprising carbamide peroxide and at least one terpene for use in inducing adipolysis at a target site in a subject.

The formulation may comprise from about 25% to about 75% by weight carbamide peroxide, based on the total weight of the formulation.

The formulation may comprise from about 25% to about 75% by weight of at least one terpene, based on the total weight of the formulation.

The at least one terpene may be at least one of d-limonene, menthol, menthone, isomenthone, menthofuran, cineole, limonene, carvone, tricyclene, α-pinene, terpinolene, carveol, amyl alcohol, nerol, β-santalol, citral, pinene, nerol, b-ionone, caryophillen, guaiol, anisaldehyde, cedrol, linalool, longifolene, anisyl alcohol, patchouli alcohol, α-cadinene, 1,8-cineole, ρ-cymene, 3-carene, ρ-8-mentane, trans-menthone, borneol, α-fenchol, isoamyl acetate, terpin, cinnamic aldehyde, ionone, geraniol, myrcene, nerol, citronellol, carvacrol, eugenol, carvone, α-terpineol, anethole, camphor, nerolidol, farnesol, phytol, carotene, squalene, thymol, tocotrienol, perillyl alcohol, borneol, simene, carene, terpenene, linalool, 1-terpene-4-ol, or zingiberene.

The formulation may comprise an injectable preparation.

The formulation may be in the form of an aqueous solution, a hydroalcoholic solution, an oil-in-water emulsion, a water-in-oil emulsion, a multiple emulsion, a cream, a suspension, a powder, a lotion, a milk, a serum, a pomade, a gel, a paste, a foam, or a transdermal patch.

The formulation may comprise at least one of a pharmaceutically acceptable carrier or diluent.

Some embodiments comprise a dermatological preparation that is effective in reducing localized subcutaneous fat deposits. In some embodiments, a dermatological preparation including (a) carbamide peroxide and a terpene, (b) carbamide peroxide and peppermint oil, or (c) carbamide peroxide and a compound isolated or derived from peppermint oil is effective in reducing localized subcutaneous fat deposits. In some embodiments, a combination of carbamide peroxide and a terpene such as d-limonene, a combination of carbamide peroxide and peppermint oil, or the combination of carbamide peroxide and a compound isolated or derived from peppermint oil have unexpectedly remarkable properties in disrupting or reducing localized subcutaneous fat deposits (i.e., they have "adipolysis inducing effects").

Some embodiments of the subject technology provide a dermatological preparation having characteristics suitable for topical or percutaneous delivery to the skin for disrupting or reducing localized subcutaneous fat deposits. Some embodiments of the subject technology provide a method for delivering a dermatological preparation of the subject technology to the skin for disrupting or reducing localized subcutaneous fat deposits.

Some dermatological preparations of the subject technology include, as a first component, carbamide peroxide and, as a second component, at least a terpene such as d-limonene. In some embodiments, the dermatological preparations of the subject technology include, as a first component, carbamide peroxide and, as a second component, a peppermint oil terpene. In some embodiments, the dermatological preparations of the subject technology include, as a first component, carbamide peroxide and, peppermint oil or a compound isolated or derived from peppermint oil. In some embodiments, the dermatological preparations of the subject technology can be applied either percutaneously or topically to the skin for disrupting or reducing localized subcutaneous fat deposits.

Some embodiments of the subject technology provide a simple, rapidly and transdermally deployable, topical preparation for the effective treatment of unwanted fat and lipodystrophies.

Some embodiments of the subject technology provide the user with a simple, non-invasive, effective, rapidly deployable composition and method for improving cosmetic appearance via the elimination of unwanted fat at target sites in the body. Exemplary target sites comprise the hips, under chin, the buttocks, the thighs, the belly or the face.

Some embodiments of the subject technology provide the user with a safe, simple, effective, and rapidly deployable composition for application to target sites comprising adipose tissues in a subject in need thereof. In some embodiments, the compositions of the subject technology induce lysis of adipose cells in a subject in need thereof, at target sites where the compositions have been administered, i.e., areas where the adipose cell aggregates are unwanted, such as the hips, under the chin, the buttocks, the thighs, the belly, or the face for example.

Some embodiments of the subject technology provide the user with a safe, simple, and effective topical preparation in the form of a cream, a lotion, an emulsion, a paste, an ointment, a transdermal patch or the like. In an embodiment, the topical preparation of the subject technology has lipo-dissolving capabilities. Some embodiments of the subject technology can induce adipolysis at a target site in the body.

Some embodiments of the subject technology provide a dermatological preparation for intradermal injection, wherein the preparation has lipo-dissolving capabilities.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof.

It is to be understood that both the foregoing general description and the following detailed description are exemplary and explanatory and are intended to provide further explanation of the subject technology as claimed.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology. In describing and claiming the subject technology, the following terminology will be used in accordance with the definitions set out below.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined, italicized, and/or boldface headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The term "isolated or derived from peppermint oil" as used herein refers to any natural compound that can be isolated from peppermint oil via conventional extraction methods, such as ethanol extraction or $CO_2$ extraction methods for example. Alternatively or in addition, the term refers to any of the peppermint oil compounds that can be synthesized de novo via one or more chemical reactions. Alternatively or in addition, the term refers to structural analogs of the peppermint oil compounds that can be derived from the natural or synthetic peppermint oil compounds via additional reactions such as isomerization, reduction, oxidation, addition, substitution, and the like. Peppermint oil is distilled from the above-ground parts of *Mentha piperita* harvested just before flowering. The oil components are: 30 to 55% menthol, 14 to 32% menthone, 2.8 to 10% menthyl acetate, 1.5 to 10% isomenthone, 1 to 9% menthofuran, 3.5 to 14% cineole, up to 4% pulegone, 1 to 5% limonene, up to 0.2% isopulegol, and up to 1% carvone.

As used herein, the terms "adipolysis" and "lipolysis of adipocytes" are used interchangeably and refer to disruption, degradation, or reduction of localized subcutaneous fat deposits, and can involve the breakdown of lipids and/or hydrolysis of triglycerides into free fatty acids followed by further degradation into acetyl units by beta oxidation. The degradation process can produce ketones, which are found in large quantities in ketosis, a metabolic state that occurs when the liver converts fat into fatty acids and ketone bodies. Lipolysis testing strips can be used to recognize ketosis.

Some compositions of the subject technology are suitable for use in the treatment of localized adiposity or conditions such as cellulite and/or sagging skin. The terms "effective amount" and "therapeutically effective amount" are used interchangeably herein and refer to an amount effective to break down human adipose tissue and thereby reduce local or regional adiposity and/or prevent and/or treat cellulite. Alternatively or additionally, these terms correspond to the quantity necessary to obtain a desired result, e.g., reduction or adipolysis of subcutaneous fat deposits in a specific target body area of a subject. An appropriate "effective amount" in any subject or individual can be determined using techniques known in the art, such as, for example, by assessing the expression levels of adiponectin receptor (Adipor1), as described in more detail below.

"Treating" and "treatment" as used herein refer to reduction in severity and/or frequency of symptoms, elimination of symptoms and/or underlying cause, prevention of the occurrence of symptoms and/or their underlying cause, and improvement or remediation of damage. These terms, as used herein, includes within their scope reducing, delaying, eliminating, and/or preventing the appearance of localized adiposity and/or cellulite, and/or generally enhancing the quality of skin by improving its appearance and/or texture. The compositions according to the subject technology may be useful for treating skin that is already suffering from localized adiposity and/or cellulite or to treat youthful skin to prevent or reduce the appearance of localized adiposity and/or cellulite.

A "treatment period" is defined as a period of time during which a treatment is administered to a subject, such as, for example, a period of time a patient is under a physician's care or direction, which may vary from patient to patient, and may be dependent on various factors including (a) metabolism of the compositions and/or the active ingredients of the subject technology administered to the patient, (b) age, weight, and general condition of the patient, (c) the severity of the condition being treated, and (d) the judgment of the prescribing physician. In some embodiments, the treatment period can comprise any number of weeks between 1 week and 52 weeks, or more than 52 weeks.

A "weekly dose" is the total amount of the compositions and/or the active ingredients administered to a patient during a single week. For example, when more than a single administration occurs during a week, the weekly dose is the total amount of the compositions and/or the active ingredients provided to the patient in each administration that occurs during the week.

A "periodic dose" is the frequency at which a dose is administered to a patient during a period.

A "single session dose" is the total amount of the compositions and/or the active ingredients administered to a patient during a single visit for treatment by a healthcare professional or, in situations of self-administration, a single session dose is the total amount of the compositions and/or the active ingredients administered to the patient by self-administration in a single session.

In some embodiments, a single session dose is divided into smaller amounts and administered to a patient in one or more "sub-doses." In some embodiments, each "sub-dose" is subcutaneously delivered to a patient by injection, e.g., using a syringe or is administered to the patient transcutaneously and/or percutaneously.

The terms "patient" and "subject" are used interchangeably herein. In some embodiments, the patient or subject is a human. In some embodiments, the patient or subject is an animal. In some embodiments, the animal is a human, a common household pet, including for example a cat or a dog, or other species of the animal kingdom.

In some embodiments, the subject technology provides a composition comprising, as active ingredients, carbamide peroxide (CAS Reg. No. 124-43-6), as a first component, and, as a second component, a terpene such as d-limonene (CAS Reg. No. 5989-27-5). In some embodiments, the subject technology provides a composition comprising, as active ingredients, carbamide peroxide as a first component and, as a second component, peppermint oil (CAS Reg. No. 8006-90-4) or a compound isolated or derived from peppermint oil. In some embodiments, the subject technology provides a composition comprising, as active ingredients, carbamide peroxide as a first component and, as a second component, a peppermint oil terpene, such as menthol, menthone, menthofuran, cineole, limonene, or carvone. In some embodiments, active ingredients of the subject technology are used for the preparation of a cosmetic and/or dermatological and/or pharmaceutical composition for disrupting or reducing subcutaneous and localized fat deposits. The compositions of the subject technology can be administered in an amount effective for inducing adipolysis or lipolysis of adipocytes in subcutaneous fat deposits in a specific target body area in a subject.

In some embodiments, the subject technology relates to a dermatological preparation including a carbamide such as carbamide peroxide as a first component and, as a second component, a terpene such as d-limonene; or peppermint oil terpene; or peppermint or a compound isolated or derived from peppermint oil, which has a lipo-dissolving or adipocytes disrupting/lytic property for disrupting or reducing the localized subcutaneous fat deposits.

In an embodiment, the dermatological preparation of the subject technology include carbamide peroxide ($CH_6N_2O_3$; CAS Reg. No. 124-43-6) and d-limonene ($C_{10}H_{16}$). Other names for carbamide peroxide may include urea hydrogen peroxide, Debrox®, Exterol®, Gly-Oxide®, Hyperol®, and Ortizon®. Carbamide peroxide can be prepared by any suitable methods known in the art. Alternatively, carbamide peroxide can be purchased from vendors such as Sigma-Aldrich.

Suitable terpenes for use in the dermatological preparations and compositions of the subject technology can include any monoterpene, sesquiterpene and/or diterpene or derivatives thereof. Acyclic, monocyclic and/or bicyclic mono-, sesqui- and/or diterpenes, and those with higher numbers of rings, can be used. A "derivative" of a terpene as used herein shall be understood to mean a terpene hydrocarbon having one or more functional groups such as terpene alcohols, terpene ethers, terpene esters, terpene aldehydes, terpene ketones and the like and combinations thereof. Here, both the trans and also the cis isomers are suitable. The terpenes as well as the terpene moiety in the derivative can contain from 6 to about 100 carbon atoms and preferably from about 10 to about 25 carbon atoms.

Representative examples of suitable terpene alcohol compounds include verbenol, eugenol, transpinocarveol, cis-2-pinanol, nopol, isoborneol, carbeol, piperitol, thymol, α-terpineol, terpinen-4-ol, menthol, 1,8-terpin, dihydro-terpineol, nerol, geraniol, linalool, citronellol, hydroxycitronellol, 3,7-dimethyl octanol, dihydro-myrcenol, tetrahydro-alloocimenol, perillalcohol, falcarindiol and any one mixture thereof.

Representative examples of suitable terpene ether and terpene ester compounds include 1,8-cineole, 1,4-cineole, isobornyl methylether, rose pyran, α-terpinyl methyl ether, menthofuran, trans-anethole, methyl chavicol, allocimene diepoxide, limonene mono-epoxide, isobornyl acetate, nonyl acetate, α-terpinyl acetate, linalyl acetate, geranyl acetate, citronellyl acetate, dihydro-terpinyl acetate, meryl acetate and any one mixture thereof.

Representative examples of terpene aldehyde and terpene ketone compounds include myrtenal, campholenic aldehyde, perillaldehyde, citronellal, citral, hydroxy citronellal, camphor, verbenone, carvenone, dihydro-carvone, carvone, piperitone, menthone, geranyl acetone, pseudo-ionone, α-ionine, iso-pseudo-methyl ionone, n-pseudo-methyl ionone, isomethyl ionone, n-methyl ionone and any one mixture thereof. Any other terpene hydrocarbons having functional groups known in the art can be used in the compositions.

In an embodiment, suitable terpenes or derivatives thereof include, but are not limited to, tricyclene, α-pinene, terpinolene, carveol, amyl alcohol, nerol, β-santalol, citral, pinene, nerol, b-ionone, caryophillen (from cloves), guaiol, anisaldehyde, cedrol, linalool, d-limonene (orange oil, lemon oil), longifolene, anisyl alcohol, patchouli alcohol, α-cadinene, 1,8-cineole, ρ-cymene, 3-carene, ρ-8-mentane, trans-menthone, borneol, α-fenchol, isoamyl acetate, terpin, cinnamic aldehyde, ionone, geraniol (from roses and other flowers), myrcene (from bayberry wax, oil of bay and verbena), nerol, citronellol, carvacrol, eugenol, carvone, α-terpineol, anethole, camphor, menthol, d-limonene, nerolidol, farnesol, phytol, carotene (vitamin A1), squalene, thymol, tocotrienol, perillyl alcohol, borneol, simene, carene, terpenene, linalool, 1-terpene-4-ol, zingiberene (from ginger) and any one mixture thereof. An exemplary list of the terpene compounds includes α-terpineol, 1-terpinen-4-ol, eugenol, menthol, geraniol, and d-limonene.

In an embodiment, the dermatological preparation of the subject technology includes carbamide peroxide ($CH_6N_2O_3$) and peppermint oil or a compound isolated or derived from peppermint oil. Compounds isolated from peppermint oil include menthol, menthone, menthyl acetate, isomenthone, menthofuran, cineole, pulegone, limonene, isopulegol or carvone. Compounds derived from peppermint oil include any synthetic or natural structural analogs of menthol, menthone, menthyl acetate, isomenthone, menthofuran, cineole, pulegone, limonene, isopulegol or carvone.

In an embodiment, the dermatological preparation of the subject technology can be used in or for the manufacture of a cosmetic and/or pharmaceutical composition, for topical use or intradermal injection use, intended for the treatment of abnormal subcutaneous fat accumulation, cellulite and/or the treatment of orange-peel skin. Cellulite is a particular configuration of adipose tissue. It indicates a quilted and padded skin appearance which corresponds, in a diagrammatic way, with an increase of the adipose tissue in certain areas of the body due to an increase in the quantity of fat, stored in the adipocytes, whose volume and number increase. At an advanced stage of cellulite formation, the skin spontaneously takes the appearance of "orange-peel skin."

In some embodiments, the dermatological preparations according to the subject technology contribute significantly to reducing the quantity of triglycerides contained in the adipocyte vacuoles. Without wishing to be bound by theory or mechanism of action, it is believed that the effect of the instant compositions is due to an increase in the phenomenon of lipolysis in the adipocytes, a mechanism which, in part, acts through an increase in the quantity of intracellular ATP, followed by an increase in the quantity of intracellular cAMP. This increase in the cAMP concentration results in an increased stimulation of triglyceride-lipase activity, an enzyme which allows the hydrolysis of triglycerides into fatty acids. Lipolysis is the reaction which eliminates triglycerides stored in the adipocytes. An increase in this phenomenon will allow a more significant elimination of triglycerides as well as an increase in the release of free fatty acid and glycerol into the extracellular medium. Thus, when the quantity of triglycerides present in the adipocyte vacuoles decreases, their volume decreases. The skin gradually takes back its "normal" appearance: the subcutaneously accumulated fat or adipose tissue is reduced, the orange-peel skin effect is attenuated, the unpleasant appearance of the body disappears.

Thus, the degree of lipolytic activity of the dermatological preparations of some embodiments of the subject technology and their capacities to act in lipolysis can vary according to the cAMP concentration. The dermatological preparations of the subject technology can, in some embodiments, allow the fatty deposits to decrease, to slow down or to resorb. The active ingredients according to some embodiments of the subject technology or the compositions containing them can have a slimming activity and can enable the appearance of the skin to improve (e.g., to look smooth and soft) and to attenuate, for example, the appearance of "orange-peel skin."

According to an aspect, the subject technology relates to a cosmetic and/or dermatological and/or pharmaceutical compositions characterized in that they contain, in an acceptable medium, as active ingredients, a carbamide such as carbamide peroxide as a first component and, as a second component, at least one terpene such as d-limonene, at least one terpene derived from peppermint oil, peppermint oil, or a compound isolated or derived from peppermint oil.

According to some embodiments, the composition of the subject technology comprises carbamide peroxide and at least one terpene. In an embodiment, the composition of the subject technology comprises carbamide peroxide and d-limonene. In an embodiment, the composition of the subject technology comprises carbamide peroxide and menthol. In an embodiment, the composition of the subject technology comprises carbamide peroxide and menthone. In an embodiment, the composition of the subject technology comprises carbamide peroxide and menthofuran. In an embodiment, the composition of the subject technology comprises carbamide peroxide and cineole. In an embodiment, the composition of the subject technology comprises carbamide peroxide and carvone. In an embodiment, the composition of the subject technology comprises carbamide peroxide and at least one of d-limonene, menthol, menthone, menthofuran, cineole or carvone. In an embodiment, the composition of the subject technology comprises carbamide peroxide and a peppermint oil terpene comprising at least one of limonene, menthol, menthone, menthofuran, cineole or carvone.

According to some embodiments, the composition of the subject technology comprises carbamide peroxide and peppermint oil or a compound isolated or derived from peppermint oil. In an embodiment, the composition of the subject technology comprises carbamide peroxide and peppermint oil. In an embodiment, the composition of the subject technology comprises carbamide peroxide and a compound isolated or derived from peppermint oil. In an embodiment, the composition of the subject technology comprises carbamide peroxide and at least one compound isolated or derived from peppermint oil. In an embodiment, the composition of the subject technology comprises carbamide peroxide and at least one of menthol, menthone, menthyl acetate, isomenthone, menthofuran, pulegone, limonene, isopulegol or carvone.

Some embodiments of the subject technology relate to a method of inducing adipolysis at a target site (i.e., the site of localized adiposity) in a subject in need thereof, said method comprising administering to the target site a therapeutically effective amount of a composition of the subject technology. One or more of the compositions of the subject technology can be used in the methods of the subject technology.

In some embodiments, the compositions of the subject technology can be administered by ingestion, injection, or, application to skin (on various cutaneous zones of the body), hair, nails or mucous membranes. In an embodiment, the compositions of the subject technology are used in pharmaceutical dosage forms or galenic forms. In an embodiment, the compositions are presented under a galenic form adapted for cutaneous topical administration. In an embodiment, the compositions are presented under a galenic form adapted for percutaneous administration. The compositions of the subject technology include all the cosmetic and dermatological forms. These compositions generally contain an acceptable cosmetic or dermatological medium, which is compatible with skin and hair. These compositions can take the form of an aqueous, hydro-alcoholic, or oil solution in oil-water emulsions, water-oil emulsions or in multiple emulsions an aqueous, hydro-alcoholic, or oily solution, oil-in-water emulsions, water-oil emulsions or in multiple emulsions. They can also be used as creams, in suspension, or as a powder, as long as it is adapted for application to skin, mucous membranes, lips and/or hair.

The compositions of the subject technology can also be more or less fluid and take the form of creams, lotions, milks, serums, ointments, shampoo, gel, paste and foam. Each of the compositions of the subject technology can also take a solid form such as a stick or transdermal patch, or can be used in aerosols. Each of the compositions of the subject technology can also be used as a skin care product and/or as make-up for skin.

Moreover, the compositions of the subject technology further comprise all additives that are usually used in carrying out the methods described or claimed herein. The compositions of the subject technology further comprise all the possible additives necessary for their formulation such as solvents, thickeners, diluents, anti-oxidants, colorants, solar filters, self-tanning products, pigments, fillers, preservatives, perfumes, odor absorbers, skin penetration enhancing compounds, pharmaceutical and cosmetic active ingredients, essential oils, vitamins, essential fatty acids, tensioactives, filmogen polymers and the like. In any case, specialists in their field will want to carefully consider the selection of additives, as well as their proportions, so as not to compromise the advantageous properties of the composition relating to the subject technology. These additives can, for example, correspond to 0.01% to 20% of the total weight of the composition. When the composition relating to the subject technology is in an emulsion, the fatty phase can represent from 5% to 80% by weight, and alternatively from 5% to 50% of the weight with respect to the total weight of the composition. Emulsifiers or co-emulsifiers used in the composition are selected among those that are classically used in the domain under consideration. For example, they can be used in a proportion of 0.3% to 30% by weight relative to the total weight of the composition. Of course, the person skilled in the art should select the complementary compounds for the composition, active or non-active, as well as the amounts of the complementary compounds in such a way that the advantageous properties of the composition will not be perceptibly altered by the envisaged addition.

Suitable solvents, thickeners, diluents, anti-oxidants, colorants, solar filters, self-tanning products, pigments, fillers, preservatives, perfumes, odor absorbers, skin penetration enhancing compounds, which may be used in the formulations of the subject technology are known in the art. For example, in addition to the active ingredients, the liquid dosage forms of the subject technology may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Exemplary preservatives, suitable for use in the formulations of the subject technology, include mercury-containing substances such as merfen and thiomersal; stabilized chlorine dioxide; and quaternary ammonium compounds such as benzalkonium chloride, cetyltrimethylammonium bromide and cetylpyridinium chloride. Exemplary antioxidants, suitable for use in the formulations of the subject technology, include ascorbic acid and sodium metabisulfite. Exemplary penetration enhancers, suitable for use in the formulations of the subject technology, include ethanol, glyceryl monoethyl ether, monoglycerides, isopropylmyristate, lauryl alcohol (also, lauric acid, lauryl lactate), terpinol, menthol, D-limonene, beta-cyclodextrin, DMSO, polysorbates, fatty acids e.g. oleic, N-methylpyrrolidone, polyglycosylated glycerides, 1-dodecylaza cycloheptan-2-one known as Azone®, cyclopentadecalactone known as CPE-215®, alkyl-2-(N,N-disubstituted amino)-alkanoate ester known as NexAct®, 2-(n-nonyl)-1,3-dioxolane known as SEPA®, or a mixture of at least two of benzyl alcohol, acetone or isopropanol.

The compositions relating to the subject technology can be applied as a cosmetic or pharmaceutical composition for skin use, mucous membranes and/or semi-mucous membranes, but also as cosmetic or pharmaceutical compositions for superficial body growths. The compositions can be applied particularly as skin protection and skin care products, or as an anti-wrinkle and/or an anti-aging composition, or as a slimming and/or toning composition.

In an embodiment, the slimming and/or toning composition of the subject technology can be applied locally to the zones of the face or the body to be slimmed, in particular to the hips, under chin, the buttocks, the thighs, the belly and the face. The compositions of the subject technology can also be suitable for application in the field of facial and body make-up compositions, such as lipsticks, foundation, tinted creams, dark circle sticks, or sunscreen and artificial tanning compositions.

The compositions of the subject technology can be used in a great number of treatments, notably cosmetic and dermatological treatments. They can take the form of cosmetic compositions for lips, skin protection, care and make-up removal and/or cleaning, as well as for make-up applications to skin, lips, eyelashes and/or the body. The compositions of the subject technology can also be used in preparations such as soap and other cleaning bar soaps. The compositions can also be made in aerosol form in which it can be mixed with pressurized propulsion agents.

The subject technology also relates to a cosmetic process in order to obtain a slimming action as well as a process of cosmetic care intended to reduce, eliminate and/or prevent overloading of subcutaneous fat, and/or intended to fight against cellulite and/or to fight against the phenomenon of orange-peel skin and/or to fight against the abnormal accumulation of subcutaneous fat deposits. This includes topically or intradermally applying an effective amount of a composition comprising, as active ingredients, a carbamide such as carbamide peroxide as a first component and, as a second component, a terpene such as d-limonene or a peppermint terpene; or peppermint oil or a compound isolated or derived from peppermint oil, to concerned zones of the skin (e.g., sites of localized adiposity).

In an embodiment, the subject technology relates to a method of inducing adipolysis at a target site in the skin of subject in need thereof, said method comprising administering to the target site a therapeutically effective amount of a composition comprising carbamide peroxide as a first component and, as a second component, at least one terpene. The terpene in the administered composition can comprise at least one of d-limonene, menthol, menthone, menthofuran, cineole or carvone. The terpene in the administered composition can comprise a peppermint terpene such as menthol, menthone, menthofuran, cineole, limonene, or carvone. The terpene in the administered composition can comprise at least one of the terpenes listed in the present disclosure.

In an embodiment, the subject technology relates to a method of inducing adipolysis at a target site in the skin of subject in need thereof, said method comprising administering to the target site a therapeutically effective amount of a composition comprising carbamide peroxide as a first component and, as a second component, peppermint oil or a compound isolated or derived from peppermint oil. In an aspect relating to this embodiment, the compound isolated or derived from peppermint oil is at least on of menthol, menthone, menthyl acetate, isomenthone, menthofuran, pulegone, limonene, isopulegol or carvone.

The process of dermatological or cosmetic treatment relating to the subject technology can be implemented in particular by applying the compositions discussed hereinabove according to methods generally used for compositions such as the application of creams, gels, serums, lotions, milks, shampoo, and sun creams, on skin, hair and as a toothpaste applied to the gums or as a transdermal patch for local administration.

In addition, the compositions of the subject technology can be administered intradermally via subcutaneous injection. Compositions of the subject technology can be introduced into the subject most conveniently by parenteral or subcutaneous injection, intramuscularly, intradermally, or orally. Any of the common liquid or solid vehicles may be employed, which are acceptable to the subject and which do not have any adverse side effects on the host or any detrimental effects on the dermatological preparation of the subject technology. Phosphate buffered saline (PBS), at physiological pH, e.g. pH 6.8 to 7.2, preferably pH 7, may be used as a carrier, alone or with a suitable excipient. The concentration of the composition of the subject technology may vary from about 0.5 to 500 µg/kg, such as about 25 µg/kg per injection, in a volume of clinical solvent generally from about 0.1 to 1 ml, such as about 0.2 ml, preclinical studies in animals, and from about 0.5 ml to about 2 ml, such as about 1 ml in humans. Multiple injections may be required after the initial injections and may be given at intervals of from about a few hours to about a few days, for example, every 2 to 6 hours, or every 2 to 4 days, or every 2 to 4 weeks, for example, about 2 weeks in animals and about 4 to 8 weeks in humans, when multiple injections are given. In an embodiment, the subject technology relates to mammals in general, and more specifically, to humans.

In an embodiment relating to an advantageous mode of realization of the subject technology, the first (e.g., carbamide peroxide) and second (e.g., d-limonene, a peppermint oil terpene, peppermint oil or a compound isolated or derived from peppermint oil) components are present in the compositions of the subject technology at a concentration from approximately about 0.005 to about 5000 ppm, or alternatively at a concentration from approximately about 0.01 to about 1000 ppm, or alternatively at a concentration from approximately about 0.05 to about 700 ppm, or alternatively at a concentration from approximately about 0.1 to about 400 ppm, or alternatively at a concentration from approximately about 0.5 to about 250 ppm, or alternatively at a concentration from approximately about 1 to about 200 ppm, or alternatively at a concentration from approximately about 0.5 to about 300 ppm, or alternatively at a concentration from approximately about 10 to about 500 ppm, or alternatively at a concentration from approximately about 0.5 to about 500 ppm, or alternatively at a concentration from approximately about 10 to about 500 ppm, or alternatively at a concentration from approximately about 1.5 to about 500 ppm relative to the total weight of the final composition.

In an embodiment relating to an advantageous mode of realization of the subject technology, the first (e.g., carbamide peroxide) and second (e.g., d-limonene, a peppermint oil terpene, peppermint oil or a compound isolated or derived from peppermint oil) components are present in the compositions of the subject technology at a concentration ranging by weight:weight or weight:volume percentages of from about 1% to about 99%, from about 1% to about 50%, from about 25% to about 75%, or from about 50% to about 99%.

In an embodiment relating to an advantageous mode of realization of the subject technology, the first (e.g., carbamide peroxide) and second (e.g., d-limonene, a peppermint oil terpene, peppermint oil or a compound isolated or derived from peppermint oil) components are each present in the compositions of the subject technology at a concentration ranging by weight:weight or weight:volume percentages of from about 1% to about 5%, about 1% to about 10%, about 10% to about 15%, about 15% to about 20%, about 20% to about 25%, about 25% to about 30%, about 30% to about 40%, about 40% to about 50%, about 50% to about 60%, about 60% to about 70%, about 70% to about 80%, about 80% to about 90%, and about 90% to about 99%, relative to total weight or volume of the compositions.

In an embodiment, the compositions of the subject technology are formulated to comprise at most about 1, 2, 3, 4, 5, 6, 7, 8, 9, 10, 11, 12, 15, 20, 25, 30, 31, 35, 40, 45, 50, 55, 60, 65, 70, 75, 80, 85, 90, 95 or 99% by weight relative to total weight of the compositions a carbamide such as carbamide peroxide as the first component of the compositions. In a related embodiment, the compositions of the subject technology are formulated to comprise at most about 1, 2, 3, 4, 5, 6, 7, 8, 9, 10, 11, 12, 15, 20, 25, 30, 31, 35, 40, 45, 50, 55, 60, 65, 70, 75, 80, 85, 90, 95 or 99% by weight relative to total weight of the compositions at least one terpene such as d-limonene, as the second component of the compositions. In a related embodiment, the compositions of the subject technology are formulated to comprise at most about 1, 2, 3, 4, 5, 6, 7, 8, 9, 10, 11, 12, 15, 20, 25, 30, 31, 35, 40, 45, 50, 55, 60, 65, 70, 75, 80, 85, 90, 95 or 99% by weight relative to total weight of the compositions a peppermint oil terpene such as menthol, menthone, menthofuran, limonene, or carvone, as the second component of the compositions. In a related embodiment, the compositions of the subject technology are formulated to comprise at most about 1, 2, 3, 4, 5, 6, 7, 8, 9, 10, 11, 12, 15, 20, 25, 30, 31, 35, 40, 45, 50, 55, 60, 65, 70, 75, 80, 85, 90, 95 or 99% by weight relative to total weight of the compositions peppermint oil or a compound isolated or derived from peppermint oil as the second component of the compositions.

In some embodiments relating to the compositions of the subject technology, an amount of a carbamide peroxide in a dose of the composition effective to induce adipolysis at a target site (i.e., the site of localized adiposity) in the body may be, in weight of administered carbamide peroxide per kilogram of mammal body weight per day (mg/kg/day), in a range of from, for instance, about 1 mg/kg/day to about 10 mg/kg/day, about 10 mg/kg/day to about 20 mg/kg/day, about 20 mg/kg/day to about 30 mg/kg/day, about 30 mg/kg/day to about 40 mg/kg/day, about 40 mg/kg/day to about 50 mg/kg/day, about 50 mg/kg/day to about 60 mg/kg/day, about 60 mg/kg/day to about 100 mg/kg/day, about 100 mg/kg/day to about 125 mg/kg/day, about 125 mg/kg/day to about 150 mg/kg/day, about 150 mg/kg/day to about 175 mg/kg/day, about 175 mg/kg/day to about 200 mg/kg/day, about 200 mg/kg/day to about 225 mg/kg/day, about 225 mg/kg/day to about 250 mg/kg/day, about 250 mg/kg/day to about 275 mg/kg/day, about 275 mg/kg/day to about 300 mg/kg/day, about 300 mg/kg/day to about 325 mg/kg/day, about 325 mg/kg/day to about 350 mg/kg/day, about 350 mg/kg/day to about 375 mg/kg/day, about 375 mg/kg/day to about 400 mg/kg/day, about 400 mg/kg/day to about 425 mg/kg/day, about 425 mg/kg/day to about 450 mg/kg/day, about 450 mg/kg/day to about 475 mg/kg/day, about 475 mg/kg/day to about 500 mg/kg/day, about 500 mg/kg/day to about 550 mg/kg/day, about 550 mg/kg/day to about 600 mg/kg/day, about 600 mg/kg/day to about 650 mg/kg/day, about 650 mg/kg/day to about 700 mg/kg/day, about 700 mg/kg/day to about 750 mg/kg/day, about 750 mg/kg/day to about 800 mg/kg/day, about 800 mg/kg/day to about 850 mg/kg/day, about 850 mg/kg/day to about 900 mg/kg/day, about 900 mg/kg/day to about 950 mg/kg/day, about 950 mg/kg/day to about 1 g/kg/day, about 1 g/kg/day to about 1.25 g/kg/day, about 1.25 g/kg/day to about 1.5 g/kg/day, about 1.5 g/kg/day to about 1.75 g/kg/day, about 1.75 g/kg/day to about 2 g/kg/day, about 2 g/kg/day to about 2.25 g/kg/day, about 2.25 g/kg/day to about 2.5 g/kg/day, about 2.5 g/kg/day to about 2.75 g/kg/day, about 2.750 g/kg/day to about 3 g/kg/day, about 3 g/kg/day to about 4 g/kg/day, about 4 g/kg/day to about 5 g/kg/day, about 5 g/kg/day to about 6 g/kg/day, about 6 g/kg/day to about 7 g/kg/day, about 7 g/kg/day to about 8 g/kg/day, about 8 g/kg/day to about 9 g/kg/day, about 9 g/kg/day to about 10 g/kg/day, and about 10 g/kg/day to about 20 g/kg/day, or any amount in between any of these ranges.

In some embodiments relating to the compositions of the subject technology, an amount of a terpene (e.g., d-limonene) in a dose of the composition effective to induce adipolysis at a target site (i.e., the site of localized adiposity) in the body may be, in weight of administered terpene per kilogram of mammal body weight per day (mg/kg/day), in a range of from, for instance, about 1 mg/kg/day to about 10 mg/kg/day, about 10 mg/kg/day to about 20 mg/kg/day, about 20 mg/kg/day to about 30 mg/kg/day, about 30 mg/kg/day to about 40 mg/kg/day, about 40 mg/kg/day to about 50 mg/kg/day, about 50 mg/kg/day to about 60 mg/kg/day, about 60 mg/kg/day to about 100 mg/kg/day, about 100 mg/kg/day to about 125 mg/kg/day, about 125 mg/kg/day to about 150 mg/kg/day, about 150 mg/kg/day to about 175 mg/kg/day, about 175 mg/kg/day to about 200 mg/kg/day, about 200 mg/kg/day to about 225 mg/kg/day, about 225 mg/kg/day to about 250 mg/kg/day, about 250 mg/kg/day to about 275 mg/kg/day, about 275 mg/kg/day to about 300 mg/kg/day, about 300 mg/kg/day to about 325 mg/kg/day, about 325 mg/kg/day to about 350 mg/kg/day, about 350 mg/kg/day to about 375 mg/kg/day, about 375 mg/kg/day to about 400 mg/kg/day, about 400 mg/kg/day to about 425 mg/kg/day, about 425 mg/kg/day to about 450 mg/kg/day, about 450 mg/kg/day to about 475 mg/kg/day, about 475 mg/kg/day to about 500 mg/kg/day, about 500 mg/kg/day to about 550 mg/kg/day, about 550 mg/kg/day to about 600 mg/kg/day, about 600 mg/kg/day to about 650 mg/kg/day, about 650 mg/kg/day to about 700 mg/kg/day, about 700 mg/kg/day to about 750 mg/kg/day, about 750 mg/kg/day to about 800 mg/kg/day, about 800 mg/kg/day to about 850 mg/kg/day, about 850 mg/kg/day to about 900 mg/kg/day, about 900 mg/kg/day to about 950 mg/kg/day, about 950 mg/kg/day to about 1 g/kg/day, about 1 g/kg/day to about 1.25 g/kg/day, about 1.25 g/kg/day to about 1.5 g/kg/day, about 1.5 g/kg/day to about 1.75 g/kg/day, about 1.75 g/kg/day to about 2 g/kg/day, about 2 g/kg/day to about 2.25 g/kg/day, about 2.25 g/kg/day to about 2.5 g/kg/day, about 2.5 g/kg/day to about 2.75 g/kg/day, about 2.750 g/kg/day to about 3 g/kg/day, about 3 g/kg/day to about 4 g/kg/day, about 4 g/kg/day to about 5 g/kg/day, about 5 g/kg/day to about 6 g/kg/day, about 6 g/kg/day to about 7 g/kg/day, about 7 g/kg/day to about 8 g/kg/day, about 8 g/kg/day to about 9 g/kg/day, about 9 g/kg/day to about 10 g/kg/day, and about 10 g/kg/day to about 20 g/kg/day, or any amount in between any of these ranges.

In some embodiments relating to the compositions of the subject technology, an amount of a peppermint oil terpene, peppermint oil, or a compound isolated or derived from peppermint oil in a dose of the composition effective to induce adipolysis at a target site (i.e., the site of localized adiposity) in the body may be, in weight of administered compound per kilogram of mammal body weight per day (mg/kg/day), in a range of from, for instance, about 1 mg/kg/day to about 10 mg/kg/day, about 10 mg/kg/day to about 20 mg/kg/day, about 20 mg/kg/day to about 30 mg/kg/day, about 30 mg/kg/day to about 40 mg/kg/day, about 40 mg/kg/day to about 50 mg/kg/day, about 50 mg/kg/day to about 60 mg/kg/day, about 60 mg/kg/day to about 100 mg/kg/day, about 100 mg/kg/day to about 125 mg/kg/day, about 125 mg/kg/day to about 150 mg/kg/day, about 150 mg/kg/day to about 175 mg/kg/day, about 175 mg/kg/day to about 200 mg/kg/day, about 200 mg/kg/day to about 225 mg/kg/day, about 225 mg/kg/day to about 250 mg/kg/day, about 250 mg/kg/day to about 275 mg/kg/day, about 275 mg/kg/day to about 300 mg/kg/day, about 300 mg/kg/day to about 325 mg/kg/day, about 325 mg/kg/day to about 350 mg/kg/day, about 350 mg/kg/day to about 375 mg/kg/day, about 375 mg/kg/day to about 400 mg/kg/day, about 400 mg/kg/day to about 425 mg/kg/day, about 425 mg/kg/day to about 450 mg/kg/day, about 450 mg/kg/day to about 475 mg/kg/day, about 475 mg/kg/day to about 500 mg/kg/day, about 500 mg/kg/day to about 550 mg/kg/day, about 550 mg/kg/day to about 600 mg/kg/day, about 600 mg/kg/day to about 650 mg/kg/day, about 650 mg/kg/day to about 700 mg/kg/day, about 700 mg/kg/day to about 750 mg/kg/day, about 750 mg/kg/day to about 800 mg/kg/day, about 800 mg/kg/day to about 850 mg/kg/day, about 850 mg/kg/day to about 900 mg/kg/day, about 900 mg/kg/day to about 950 mg/kg/day, about 950 mg/kg/day to about 1 g/kg/day, about 1 g/kg/day to about 1.25 g/kg/day, about 1.25 g/kg/day to about 1.5 g/kg/day, about 1.5 g/kg/day to about 1.75 g/kg/day, about 1.75 g/kg/day to about 2 g/kg/day, about 2 g/kg/day to about 2.25 g/kg/day, about 2.25 g/kg/day to about 2.5 g/kg/day, about 2.5 g/kg/day to about 2.75 g/kg/day, about 2.750 g/kg/day to about 3 g/kg/day, about 3 g/kg/day to about 4 g/kg/day, about 4 g/kg/day to about 5 g/kg/day, about 5 g/kg/day to about 6 g/kg/day, about 6 g/kg/day to about 7 g/kg/day, about 7 g/kg/day to about 8 g/kg/day, about 8 g/kg/day to about 9 g/kg/day, about 9 g/kg/day to about 10 g/kg/day, and about 10 g/kg/day to about 20 g/kg/day, or any amount in between any of these ranges.

In clinical studies, an effective amount of the compositions and/or the active ingredients (e.g., a carbamide such as carbamide peroxide as a first component and, as a second component, (a) a terpene such as d-limonene or a peppermint oil terpene, (b) peppermint oil, or (c) a compound isolated or derived from peppermint oil) of the subject technology can be determined by assessing whether a decrease in blood plasma triglycerides is detectable upon treatment of the subject with the compositions and/or the active ingredients of the subject technology. In a related embodiment, a reduction in plasma levels of triglycerides indicates fat breakdown, which can result from treatment of a patient with multiple, relatively small injections or applications of the compositions of the subject technology within or on an area of the patient's fat stores. For example, the injectable dose can include about 0.1 to 0.5 mg of each or both of the active ingredients of the subject technology in a volume of about 0.5 ml injection grade solution, such as water.

In an embodiment, an effective amount of the compositions and/or the active ingredients of the subject technology can be determined by assessing the cAMP levels in the subject being treated with the methods and compositions of the subject technology. The natural fat break-down achieved with the present compositions/preparations may also be characterized by the increase in cAMP levels that result as a consequence of treatment. Thus, in some embodiments, an adipolysis-promoting amount of the compositions and/or the active ingredients of the subject technology may be described as an amount of the composition and/or first component and the second component that is sufficient to increase levels of cAMP in a culture of 3T3 adipocytes, compared to cAMP levels in a culture of 3T3 adipocytes without the same amount of the composition and/or the first component. By way of example, an amount of the composition and/or the first component and the second component that can increase cAMP levels could be about 11 moles/Liter.

In an embodiment, an effective amount of the compositions and/or the active ingredients of the subject technology can be determined by assessing the levels of Hormone Sensitive Lipase (HSL). The natural fat break-down achieved with the present compositions/preparations may also be characterized by the increase in hormone sensitive lipase (HSL) levels that result as a consequence of treatment with the active ingredients of the subject technology. Thus, in some embodiments, an adipolysis-promoting amount of the compositions and/or the active ingredients of the subject technology can be described as an amount that increases detectable amounts of hormone sensitive lipase (HSL) in a culture of 3T3 adipocytes, compared to hormone sensitive lipase (HSL) levels in a culture of 3T3 adipocytes without the same amount of the compositions and/or the active ingredients. In some embodiments, this may be described as an amount of the compositions and/or the active ingredients of the subject technology that increases expression of a gene encoding hormone sensitive lipase (HSL). By way of example, the amount of the compositions and/or the active ingredients of the subject technology that increases detectable amounts of hormone sensitive lipase in a culture of 3T3 adipocytes compared to the amount of hormone sensitive lipase detectable in a culture of 3T3 adipocytes without the same compositions and/or the active ingredients is about 1 mmol/Liter.

In an embodiment, an effective amount of the compositions and/or the active ingredients of the subject technology can be determined by assessing the adipolysis-promoting ratio of adrenergic receptor (AR) expression (lipolysis greater than lipogenesis), β-adrenergic receptors/a2b-adrenergic receptor expression ratio. The natural fat break-down achieved with the present compositions/preparations may also be characterized by the increase in expression levels of β-adrenergic receptors that result as a consequence of treatment. Therefore, in some embodiments, the adipolysis-promoting amount of the compositions and/or the active ingredients of the subject technology may be described as an amount that is sufficient to provide a lipolysis enhancing ratio of adrenergic receptor expression, relative to lipogenesis enhancing adrenergic receptor expression in a culture of 3T3 adipocytes without or in absence of the same amount of the compositions and/or the active ingredients. By way of example, the lipolysis enhancing adrenergic receptors include Adrb1, Adrb2 and Adrb3, while the lipogenesis enhancing adrenergic receptors include a2B-AR.

Generally, the compositions and/or the active ingredients of the subject technology would be provided in an amount that would elicit a lipolysis enhancing ratio of adrenergic receptor expression. By way of example, this amount would comprise an increase in the ratio of β-adrenergic receptor expression relative to a2b-adrenergic receptor expression. This amount of the compositions and/or the active ingredients of the subject technology may further be described as an amount that results in an increase in 3-fold to about 7 or 8-fold expression of the lipolysis enhancing adrenergic receptors, relative to the expression level of a2b-adrenergic receptors.

In an embodiment, an effective amount of the compositions and/or the active ingredients of the subject technology can be determined by assessing the expression levels of adiponectin receptor (Adipor1). The natural fat break-down achieved with the present compositions/preparations may also be characterized by a decrease in expression levels of adiponectin receptor (Adipor1) that results as a consequence of treatment. Therefore, and in some embodiments, the adipolysis-promoting amount of the compositions and/or the active ingredients of the subject technology may be described as an amount that is sufficient to provide a decrease or reduction in the expression of Adipor1 in a culture of 3T3 adipocytes relative to the amount of Adipor1 expression in a culture of 3T3 adipocytes without the same amount of the compositions and/or the active ingredients.

In an embodiment, an effective amount of the compositions and/or the active ingredients of the subject technology can be determined by assessing the expression levels of the Obesity-Related gene panel. Carboxypeptidase E gene (Cpe gene), peroxisome proliferator activated receptor gamma gene (Pparg, a regulator of adipocyte differentiation), adrenergic receptor genes (such as Adrb2, Adrb3) and Adiponectin receptor 1 gene (Adipor1) are among some of the obesity-related genes that comprise the obesity-related gene panel.

In some embodiments, an adipolysis-promoting amount of the compositions and/or the active ingredients of the subject technology may be described as an amount that increases the expression level of a panel of obesity-related genes relative to the expression level of the same panel of obesity-related genes in the absence of the same amount of the compositions and/or active ingredients. In some embodiments, an adipolysis-promoting amount of the compositions and/or the active ingredients of the subject technology increases the expression level of the obesity-related gene panel by at least about 1.5 fold, compared to the expression level of this obesity-related gene panel in a culture of 3T3 adipocytes without the same amount of the compositions and/or the active ingredients.

By way of example, one obesity-related gene as described in the present methods and compositions encodes carboxypetidase E (Cpe). In particular, an adipolysis-promoting amount of the compositions and/or the active ingredients of the subject technology may be described as an amount that increases the expression level of a Cpe gene by 3T3 adipocytes, compared to the expression level of Cpe gene in a culture of 3T3 adipocytes without the same amount of the compositions and/or the active ingredients. By way of example, the amount of the compositions and/or the active ingredients of the subject technology that increases the expression level of Cpe gene by 3T3 adipocytes can be an amount that will increase expression levels of Cpe gene by at least about 2 to 3 fold compared to the expression level of Cpe gene in a culture of 3T3 adipocytes without the same amount of the compositions and/or the active ingredients. In some embodiments, this amount of the compositions and/or the active ingredients of the subject technology is about 1 μmol/Liter.

In some embodiments, the subject technology relates to pharmaceutical formulations that are suitable for subcutaneous or transcutaneous administration. In some embodiments, the pharmaceutical formulations provided herein are suitable for subcutaneous injection, and provide for a volume of up to about 20 mL (including, e.g., about 0.1 mL, about 0.3 mL, about 0.5 mL, about 0.7 mL, about 1.0 mL, about 1.1 mL, about 1.5 mL, about 2 mL, about 2.5 mL, about 3 mL, about 3.5 mL, about 4 mL, about 5 mL, about 6 mL, about 7 mL, about 8 mL, about 9 mL, or any other volume from about 0.1 mL to about 20 mL) of an excipient compatible with subcutaneous administration. In some embodiments, the excipient concentration is kept below 1% (e.g., about 0.05%, about 0.2%, about 0.3%, about 0.4%, about 0.5%, about 0.6%, about 0.8%, or any other concentration from about 0.05% to less than about 1%.

In some embodiments, the formulations and methods of treatment provided herein are based on a periodic dosing schedule.

Periodic dosing comprises administering a single session dose to a patient at intervals during a period. For example, in some embodiments, the periodic dose is once per week, and hence in these situations a patient will receive a single session dose once per week. In an embodiment, the periodic dose is 2-7 times per week (including any interval between 2 and 7), 3-6 times per week (including any interval between 3 and 6), or 4-5 days per week. In some embodiments, the periodic dose is 1-4 times per month (including any interval between 1 and 4), 2-3 times per month, or once or twice per month. In some embodiments, the periodic dose is 1-52 times per year (including any interval between 1 and 52).

Although some periodic dosing described herein is described as a dosage per week, in situations where the frequency of administration sessions is different than once per week, the weekly dosage amount can be administered at other intervals and the session dosage adjusted based on the different administration interval in some embodiments. For example, if administering a weekly dose though twice per week periodic dosing, the patient could receive the equivalent of a weekly single session dose in two separate halves (that are about equal or unequal) during the week compared to what is provided herein. Similarly, in some situations where the periodic dose is seven times per week, the amount of active ingredient administered to the patient for each single session dose compared to what is provided herein can be divided by seven. As an example, where a periodic dose is desired to be administered once per month, the patient can receive a single session dose once per month equivalent to four times the amount that is described herein as a dosage per week.

In an aspect, the formulations and methods of treatment provided herein are based on a single session dose. A single session dose is the total amount of active ingredient administered to a patient during a single visit for treatment by a healthcare professional or, in situations of self-administration, it is the amount of active ingredient administered to the patient by self-administration in a single session. The single session doses provided herein are based on a once per week periodic dose, and can be adjusted for a periodic doses at intervals other than once per week. In some embodiments a single session dose includes 20 or more sub-doses.

In an embodiment, provided herein is a subcutaneous injectable formulation that comprises a single session dose of the compositions of the subject technology of between about 20 µg and about 50 mg, including any other amount of the compositions between about 20 µg and about 50 mg.

In some embodiments, pharmaceutical formulations are formulated to provide a daily dose of the compositions of the subject technology. In some embodiments, an adipose tissue-reducing amount of the compositions to of the subject technology to be administered is about 0.001 µg/day to about 1000 µg/day (including any dose of the compositions from about 0.001 µg/day to about 1000 µg/day).

In some embodiments, the single session dose is administered to the patient in sub-doses (e.g., by subcutaneous injection, transcutaneous application, or otherwise). Accordingly, in an aspect, the single session dose amounts disclosed herein can be administered to a patient in at least two sub-doses, the total amount of which is equivalent to the single session dose, in a single session.

In some embodiments, each sub-dose can be administered to a patient by a single injection of the formulations or compositions of the subject technology. For example, a single session dose can be administered to a patient in two sub-doses, three sub-doses, four sub-doses, five sub-doses, six sub-doses, seven sub-doses, eight sub-doses, nine sub-doses, 10 sub-doses, 11 sub-doses, 12 sub-doses, 13 sub-doses, 14 sub-doses, 15 sub-doses, 16 sub-doses, 17 sub-doses, 18 sub-doses, 19 sub-doses, 20 sub-doses, 21 sub-doses, 22 sub-doses, 23 sub-doses, 24 sub-doses, 25 sub-doses, 26 sub-doses, 27 sub-doses, 28 sub-doses, 29 sub-doses, 30 sub-doses, 31 sub-doses, 32 sub-doses, 33 sub-doses, 34 sub-doses, 35 sub-doses, or more than 35 sub-doses.

In some embodiments, each sub-dose is administered to a patient in an equal amount. For example, in some situations where the single session dose is about 20 mg of a composition of the subject technology that is delivered to the patient in 20 sub-doses, each sub-dose contains about 1 mg of the composition.

In some embodiments, at least two sub-doses of a composition of the subject technology are administered to a patient in a single session dose via subcutaneous injection to the abdominal region of the patient. In an embodiment, each sub-dose is applied to a patient about 2-6 cm away from a closest second sub-dose. In an embodiment, each sub-dose is applied to a patient about 4 cm away from a closest second sub-dose.

In some embodiments, a sub-dose is administered, for example by subcutaneous or transcutaneous injection, to areas of non-visceral fat deposits on a subject, including subcutaneous fat for example. Some target locations for which the formulations described herein are useful include, but are not limited to, the inside region of the knees, the middle to upper area of the upper arm (including the triceps area), the submental area (including the area under the chin, for example the wattle or fleshy fold of skin in the submental area of a patient), the abdomen, the hips, the inner thigh, the outer thigh, the buttocks, the lower back, upper back, and the chest.

In some embodiments, administration schedules of a pharmaceutical formulation (e.g., comprising a carbamide such as carbamide peroxide as a first component and, as a second component, at least one of (a) a terpene such as d-limonene or a peppermint oil terpene, (b) peppermint oil, or (c) a compound isolated or derived from peppermint oil) effective to result in adipolysis at a target site in a subject in need thereof involve administering the formulation once per day, twice per day, three times per day, four times per day, five times per day, six times per day, seven times per day, eight times per day, nine times per day, 10 times per day, 11 times per day, 12 times per day, 13 times per day, 14 times per day, 15 times per day, 16 times per day, 17 times per day, 18 times per day, 19 times per day, 20 times per day, 21 times per day, 22 times per day, 23 times per day, 24 times per day, and continuously. In some embodiments, daily or continuous administration of a pharmaceutical formulation of the subject technology may comprise a period of at least one day, two days, three days, four days, five days, six days, seven days, two weeks, three weeks, one month, two months, three months, four months, five months, six months, seven months, eight months, nine months, 10 months, 11 months, one year, two years, three years, four years, and five years. In some embodiments, daily or continuous administration of the pharmaceutical formulation may be intermittent within an administration period, for instance, every other day, every third day, every fourth day, every fifth day, every sixth day, once a week, once every two weeks, once every three weeks, once a month, once every two months, once every three months, once every four months, once every five months, once every six months, once every seven months, once every eight months, once every nine months, once every 10 months, once every 11 months, and once a year.

Injectable formulations can be administered using any mean known in the art, for example, using a single needle, multiple needles, and/or using a needleless injection device. In some embodiments, a tissue loading dose of the compositions or the active ingredients formulated in a suitable carrier delivered by injection. In some embodiments, delivery comprises single needle injection. In some embodiments, delivery comprises injection using a multi-needle array, which, in some embodiments, provides a wide dispersion of the formulation in the target tissue. In some embodiments, formulations are injected in a manner that allows dispersal into the appropriate layer of subcutaneous fat in areas where regional fat reduction is desired, such as the submental region, the waist/hip, the lateral buttocks or thigh, or the periorbital fat regions for example. In some embodiments, the formulation is injected in aliquots of from about 0.5 mL to about 1.0 mL. In some embodiments, aliquots of the formulation are injected over an area of from about 10 cm$^2$ to about 20 cm$^2$.

Another delivery mode comprises a needleless pressurized injection device. In some embodiments, of these devices, the formulation is pressurized mechanically or pneumatically, for example, using a gas such as helium or carbon dioxide, and then forced through a small orifice into the body tissues, thereby delivering the formulation subcutaneously. Suitable formulations for needleless injection are known in the art, for example, liquid, solutions, suspensions, gels, colloids, emulsions, and dry powders. An advantage of this system is a wide dispersal area compared with typical needle injection systems. Needleless injection under the appropriate pressure forces the formulation into a more planar delivery pattern, with fingers of formulation spreading out radially following paths of least resistance. In contrast, delivery by a typical needle injection results in a globular delivery of the formulation. Needleless injection also permits precise control of the depth of penetration by controlling the injection pressure and orifice size. Thus, needleless injection can be a particularly beneficial delivery method for a sub-dermal injection of a formulation for treating superficial fat accumulations, which is useful, for example, for smoothing skin dimpling caused by fat. In some embodiments, needleless injection can be used for deeper, sub-dermal sub-fascial injections targeting deeper fat accumulations. A needleless device also provides easy and convenient multiple injections of the formulation over a defined region with a large lateral spread.

In some embodiments, an effective dose of a pharmaceutical formulation of subject technology results in elevated levels of carbamide peroxide, terpene, peppermint oil terpenes, peppermint oil, and/or compounds isolated or derived from peppermint oil in the tissue or at a target site, which is sustained for a period of, for instance, at least about one hour, about two hours, about three hours, about four hours, about five hours, about six hours, about seven hours, about eight hours, about nine hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments, an effective dose of a pharmaceutical formulation disclosed herein results in a regression in a size, e.g. a diameter, a thickness, and/or a volume (of a localized adiposity which is being treated), in a range of from, for instance, about 1% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, and about 90% to about 100%.

In some embodiments, sustained levels of an effective dose of a pharmaceutical formulation of the subject technology are effective to dissolve, disrupt, or reduce, for example, about 1% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, and about 90% to about 100% of the localized subcutaneous fat deposits at a target site (i.e., the site of localized adiposity) in the body.

In some embodiments, the tissue concentrations of an effective dose of a pharmaceutical formulation of the subject technology are effective to dissolve, disrupt, or reduce, for example, about 1% to about 5%, about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, and about 90% to about 100% of the localized subcutaneous fat deposits at a target site (i.e., the site of localized adiposity) in the body.

Other advantages and characteristics of the subject technology will become apparent to one of ordinary skill in the art by reading the above description or the following exemplary formulations, by way of an illustrative and unrestricted demonstration of data.

Several exemplary topical or injectable formulations of the subject technology are listed in Tables 1 to 8.

TABLE 1

Exemplary formulations 1-3 with carbamide peroxide and d-limonene as active ingredients.

| Component | Formula 1 Amount (wt. %) | Formula 2 Amount (wt. %) | Formula 3 Amount (wt. %) |
|---|---|---|---|
| boric acid | 0.1 | 1 | 0.64 |
| sodium borate | 0.01 | 0.2 | 0.1 |
| sodium chloride | 0.2 | 0.8 | 0.49 |
| zwitergent ® 3-10 | 0.005 | 0.8 | 0.1 |
| hyaluronic acid | 0.005 | 0.2 | 0.02 |
| d-limonene | ~0.5%-~95% | ~0.5%-~95% | ~50% |
| Carbamide peroxide | ~0.5%-~95% | ~0.5%-~95% | ~50% |
| Na2EDTA | 0.005 | 0.15 | 0.03 |

TABLE 2

Exemplary formulations 4-6 with carbamide peroxide and d-limonene as active ingredients.

| Component | Formula 4 Amount (wt. %) | Formula 5 Amount (wt. %) | Formula 6 Amount (wt. %) |
|---|---|---|---|
| sorbitol or xylitol | 0.5 | 5 | 3 |
| poloxamer 407 | 0.05 | 1 | 0.1 |
| Na diphosphate, | 0.1 | 0.8 | 0.46 |
| dexpanthenol | 0.01 | 1 | 0.03 |
| zwitergent ® 3-10 | 0.01 | 0.2 | 0.05 |
| arabinogalactan | 0.05 | 0.4 | 0.1 |
| d-limonene | ~0.5%-~95% | ~0.5%-~95% | ~50% |
| Carbamide peroxide | ~0.5%-~95% | ~0.5%-~95% | ~50% |
| Na2EDTA | 0.005 | 0.15 | 0.03 |

TABLE 3

Exemplary formulations 7-9 with carbamide peroxide and d-limonene as active ingredients.

| Component | Formula 7 Amount (wt. %) | Formula 8 Amount (wt. %) | Formula 9 Amount (wt. %) |
| --- | --- | --- | --- |
| propylene glycol | 0.1 | 1 | 0.5 |
| poloxamer 237 | 0.01 | 0.2 | 0.05 |
| Na monophosphate | 0.05 | 0.4 | 0.1 |
| Na diphosphate | 0.05 | 0.4 | 0.12 |
| zwitergent ® 3-10 | 0.01 | 0.3 | 0.1 |
| d-limonene | ~0.5%-~95% | ~0.5%-~95% | ~50% |
| Carbamide peroxide | ~0.5%-~95% | ~0.5%-~95% | ~50% |
| Na2EDTA | 0.005 | 0.3 | 0.1 |

TABLE 4

Exemplary formulations 10-12 with carbamide peroxide and d-limonene as active ingredients.

| Component | Formula 10 Amount (wt. %) | Formula 11 Amount (wt. %) | Formula 12 Amount (wt. %) |
| --- | --- | --- | --- |
| propylene glycol | 0.2 | 2 | 0.6 |
| poloxamine 1304 | 0.01 | 0.2 | 0.05 |
| boric acid | 0.1 | 1 | 0.6 |
| Na borate | 0.01 | 0.2 | 0.1 |
| hydroxypropyl guar | 0.01 | 0.4 | 0.05 |
| d-limonene | ~0.5%-~95% | ~0.5%-~95% | ~50% |
| Carbamide peroxide | ~0.5%-~95% | ~0.5%-~95% | ~50% |
| zwitergent ® 3-10 | 0.01 | 0.2 | 0.05 |
| Na2EDTA | 0.02 | 0.1 | 0.05 |

TABLE 5

Exemplary formulations 1-3 with carbamide peroxide and at least one peppermint oil terpene, or peppermint oil, or a compound isolated or derived from peppermint oil as active ingredients.

| Component | Formula 1 Amount (wt. %) | Formula 2 Amount (wt. %) | Formula 3 Amount (wt. %) |
| --- | --- | --- | --- |
| boric acid | 0.1 | 1 | 0.64 |
| sodium borate | 0.01 | 0.2 | 0.1 |
| sodium chloride | 0.2 | 0.8 | 0.49 |
| zwitergent ® 3-10 | 0.005 | 0.8 | 0.1 |
| hyaluronic acid | 0.005 | 0.2 | 0.02 |
| d-limonene | ~0.5%-~95% | ~0.5%-~95% | ~50% |
| Carbamide peroxide | ~0.5%-~95% | ~0.5%-~95% | ~50% |
| Na2EDTA | 0.005 | 0.15 | 0.03 |

TABLE 6

Exemplary formulations 4-7 with carbamide peroxide and at least one peppermint oil terpene, or peppermint oil, or a compound isolated or derived from peppermint oil as active ingredients.

| Component | Formula 4 Amount (wt. %) | Formula 5 Amount (wt. %) | Formula 6 Amount (wt. %) |
| --- | --- | --- | --- |
| sorbitol or xylitol | 0.5 | 5 | 3 |
| poloxamer 407 | 0.05 | 1 | 0.1 |
| Na diphosphate, | 0.1 | 0.8 | 0.46 |
| dexpanthenol | 0.01 | 1 | 0.03 |
| zwitergent ® 3-10 | 0.01 | 0.2 | 0.05 |
| arabinogalactan | 0.05 | 0.4 | 0.1 |
| at least one peppermint oil terpene, or peppermint oil, or a compound isolated or derived from peppermint oil | ~0.5%-~95% | ~0.5%-~95% | ~50% |
| Carbamide peroxide | ~0.5%-~95% | ~0.5%-~95% | ~50% |
| Na2EDTA | 0.005 | 0.15 | 0.03 |

TABLE 7

Exemplary formulations 7-9 with carbamide peroxide and at least one peppermint oil terpene, or peppermint oil, or a compound isolated or derived from peppermint oil as active ingredients.

| Component | Formula 7 Amount (wt. %) | Formula 8 Amount (wt. %) | Formula 9 Amount (wt. %) |
| --- | --- | --- | --- |
| propylene glycol | 0.1 | 1 | 0.5 |
| poloxamer 237 | 0.01 | 0.2 | 0.05 |
| Na monophosphate | 0.05 | 0.4 | 0.1 |
| Na diphosphate | 0.05 | 0.4 | 0.12 |
| zwitergent ® 3-10 | 0.01 | 0.3 | 0.1 |
| at least one peppermint oil terpene, or peppermint oil, or a compound isolated or derived from peppermint oil | ~0.5%-~95% | ~0.5%-~95% | ~50% |
| Carbamide peroxide | ~0.5%-~95% | ~0.5%-~95% | ~50% |
| Na2EDTA | 0.005 | 0.3 | 0.1 |

TABLE 8

Exemplary formulations 10-12 with carbamide peroxide and at least one peppermint oil terpene, or peppermint oil, or a compound isolated or derived from peppermint oil as active ingredients.

| Component | Formula 10 Amount (wt. %) | Formula 11 Amount (wt. %) | Formula 12 Amount (wt. %) |
| --- | --- | --- | --- |
| propylene glycol | 0.2 | 2 | 0.6 |
| poloxamine 1304 | 0.01 | 0.2 | 0.05 |
| boric acid | 0.1 | 1 | 0.6 |
| Na borate | 0.01 | 0.2 | 0.1 |
| hydroxypropyl guar | 0.01 | 0.4 | 0.05 |
| at least one peppermint oil terpene, or peppermint oil, or a compound isolated or derived from peppermint oil | ~0.5%-~95% | ~0.5%-~95% | ~50% |
| Carbamide peroxide | ~0.5%-~95% | ~0.5%-~95% | ~50% |
| zwitergent ® 3-10 | 0.01 | 0.2 | 0.05 |
| Na2EDTA | 0.02 | 0.1 | 0.05 |

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method of inducing adipolysis at a target site in a subject, comprising: administering to the target site in a subject who would benefit from such treatment a therapeutically effective amount of a formulation comprising carbamide peroxide and d-limonene, wherein a subcutaneous fat deposit is disrupted or degraded.

2. The method of claim 1, wherein the formulation comprises from about 1% to about 50% by weight carbamide peroxide, based on the total weight of the formulation.

3. The method of claim 1, wherein the formulation comprises from about 1% to about 50% by weight d-limonene, based on the total weight of the formulation.

4. The method of claim 1, wherein administering the formulation comprises injecting the therapeutically effective amount of the formulation at the target site.

5. The method of claim 4, wherein the administration comprises multiple injection sessions.

* * * * *